(12) United States Patent
Takeuchi

(10) Patent No.: US 9,924,951 B2
(45) Date of Patent: Mar. 27, 2018

(54) CUTTING INSTRUMENT

(71) Applicant: Smith & Nephew, Inc., Memphis, TN (US)

(72) Inventor: Yoshiro Takeuchi, Osaka (JP)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 15/593,118

(22) Filed: May 11, 2017

(65) Prior Publication Data

US 2017/0303933 A1  Oct. 26, 2017

Related U.S. Application Data

(63) Continuation of application No. 14/004,398, filed as application No. PCT/US2012/028750 on Mar. 12, 2012, now Pat. No. 9,655,629.

(30) Foreign Application Priority Data

Mar. 11, 2011  (JP) .................................. 2011-053838
Aug. 4, 2011   (JP) .................................. 2011-170653

(51) Int. Cl.
*A61B 17/00*  (2006.01)
*A61B 17/16*  (2006.01)

(52) U.S. Cl.
CPC .......... *A61B 17/16* (2013.01); *A61B 17/1617* (2013.01); *A61B 17/1624* (2013.01); *A61B 17/1631* (2013.01); *A61B 17/1675* (2013.01)

(58) Field of Classification Search
None
See application file for complete search history.

(56) References Cited

U.S. PATENT DOCUMENTS 5,591,170 A   1/1997  Spievack
5,817,095 A  10/1998  Smith
(Continued)

FOREIGN PATENT DOCUMENTS

| EP | 1785103    | 5/2007  |
|----|------------|---------|
| JP | 2002306517 | 10/2002 |
| JP | 4801225    | 10/2011 |

OTHER PUBLICATIONS

CN Office Action for CN app No. 201380072359.3 dated Jul. 14, 2017, 3 pages.

(Continued)

*Primary Examiner* — Sameh Boles
(74) *Attorney, Agent, or Firm* — Burns & Levinson, LLP; Joseph M. Maraia

(57) ABSTRACT

Provided is a cutting instrument including: an elongated member including a tubular portion 105 and a shaft-like portion 101 inserted in the tubular portion 105; a blade 201 including two edges, the blade 201 being provided at an end of the elongated member and being pivotable between a housed position and a projected position; and a motion mechanism that converts a relative movement of the tubular portion 105 and the shaft-like portion 101 resulting from an operation of an operation portion 102 to 104 into pivoting of the blade between the housed position and the projected position, wherein the cutting instrument moves toward the operation portion while rotating in its entirety with the two edges of the blade 201 projected on opposite sides of the tubular portion 105, thereby drilling a hole with a diameter larger than an outer diameter of the tubular portion 105.

16 Claims, 20 Drawing Sheets

(56) References Cited

U.S. PATENT DOCUMENTS

| | | | |
|---|---|---|---|
| 6,036,695 A | 3/2000 | Smith | |
| 2001/0008979 A1 | 7/2001 | Bonutti | |
| 2002/0032447 A1 | 3/2002 | Weikel | |
| 2004/0199166 A1 | 10/2004 | Schmieding | |
| 2004/0208717 A1 | 10/2004 | Greenhalgh | |
| 2005/0240193 A1 | 10/2005 | Reiley | |
| 2007/0123921 A1 | 5/2007 | Ek | |
| 2008/0221505 A1 | 9/2008 | Betts | |
| 2009/0228013 A1 | 9/2009 | Ferragamo | |
| 2010/0168750 A1 | 7/2010 | Sherman | |
| 2011/0144678 A1* | 6/2011 | Slater | A61B 17/3201 606/170 |
| 2013/0184610 A1 | 7/2013 | Bourque | |

OTHER PUBLICATIONS

EP Office Action for EP App No. 13735099.7 dated Aug. 4, 2017, 6 pages.
EP Office Action for EP App No. 13811705.6 dated Jul. 11, 2017, 4 pages.
JP Office Action for JP App No. 2015-511564 dated Jul. 24, 2017, 3 pages.

* cited by examiner

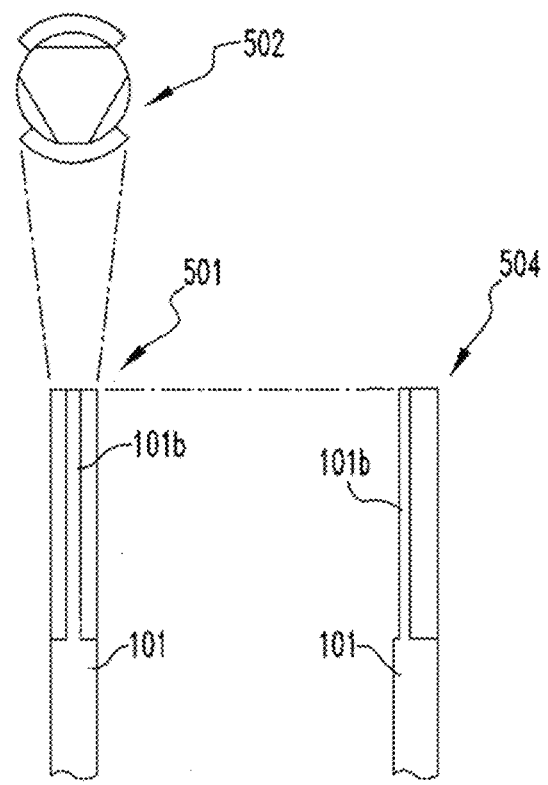
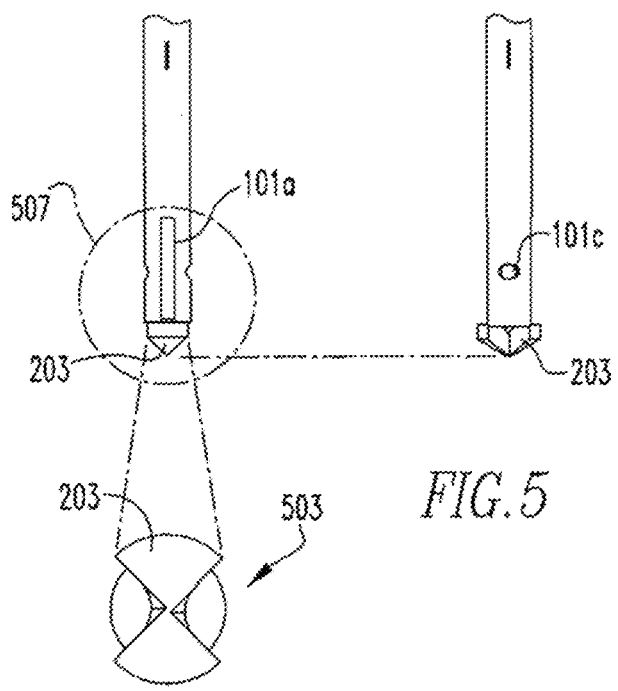
FIG. 5

CUTTING INSTRUMENT

CROSS-REFERENCE TO RELATED APPLICATIONS

This application is a continuation of U.S. patent application Ser. No. 14/004,398, filed Dec. 20, 2013 which is a National Stage Entry of International Application No. PCT/US2012/028750, filed Mar. 12, 2012, which claims priority to Japanese Application No. 2011-170653, filed Aug. 4, 2011 and also claims priority to Japanese Application No. 2011-053838, filed Mar. 11, 2011, the disclosures of which are incorporated herein by reference in their entireties for all purposes.

BACKGROUND

Field of Technology

The present disclosure relates to a cutting technique for creating a hole in a solid body.

Background Art

Conventionally, there are various cutting instruments. Among them, drills for drilling of bone are subject to restrictive conditions such as being less-invasive and being used in a limited space in a body, and thus, are often required to have special functions.

For example, Patent Literatures 1 to 4 each disclose a method for forming a hole with a large diameter (hole allowing a tendon transplant to be inserted therein) inside a joint by pulling the cutting instrument in arthroscopic surgery, and a cutting instrument thereafter.

CITATION LIST

Patent Literature

[Patent Literature 1] US Patent Publication No. US2010/0168750A1
[Patent Literature 2] US Patent Publication No. US2009/0275950A1
[Patent Literature 3] EP Patent Publication No. EP2098177A1
[Patent Literature 4] EP Patent No. 1987766

SUMMARY OF INVENTION

Problems to be Solved by the Invention

However, the aforementioned conventional techniques each have a blade only on one side of a shaft of a rotating body, and thus, are poor in cutting efficiency and balance, causing vibration and failures.

An object of the present invention is to provide a technique that solves the aforementioned problems.

Means for Solving the Problems

In order to achieve the above object, a cutting instrument according to the present invention provides
a cutting instrument including:
an elongated member including a tabular portion and a shaft-like portion inserted in the tubular portion;
a blade including two edges and a center portion connecting the two edges, the blade being provided at an end of the elongated member and being pivotable between a housed position where the blade is housed in the elongated member and a projected position where the two edges are projected outside the elongated member, with the center portion as a pivot center;
an operation portion provided at another end of the elongated member, the operation portion moving the tubular portion and the shaft-like portion relative to each other; and
a motion mechanism that converts a relative movement of the tubular portion and the shaft-like portion resulting from an operation of the operation portion into pivoting of the blade between the housed position and the projected position,
wherein the motion mechanism includes
a groove portion provided in the blade, and
a protruded portion provided at the tubular portion, the protruded portion giving a pivoting force to the blade while moving within the groove portion; and
wherein the cutting instrument moves toward the operation portion while rotating in its entirety with the two edges of the blade projected on opposite sides of the tubular portion, thereby drilling a hole with a diameter larger than an outer diameter of the tubular portion.

In order to achieve the above object, a cutting instrument according to the present invention includes:
no elongated member including a tubular portion, and a shaft-like portion inserted in the tubular portion;
a blade provided at an end of the elongated member, the blade including a pivot axis in a center thereof, and including an edge at each of two positions with the pivot shaft interposed therebetween;
an operation portion provided at another end of the elongated member, the operation portion linearly moving the tubular portion and the shaft-like portion relative to each other; and
a motion mechanism that converts a relative linear movement or the tubular portion and the shaft-like portion resulting from an operation of the operation portion into pivoting of the blade, the blade thereby pivoting between a housed position where the blade is housed in the elongated member, and a projected position where the edges are projected in two directions outside the elongated member,
wherein the elongated member is moved toward the operation portion while being rotated with the edges of the blade projected from the elongated member, thereby drilling a hole having a diameter larger than an outer diameter of the tubular portion.

Advantageous Effect of Invention

The present invention enables achievement of cutting with a high cutting efficiency and a high stability.

BRIEF DESCRIPTION OF DRAWINGS

FIG. 5 includes diagrams each illustrating a configuration of a shaft-like portion according to the first embodiment of the present invention.

FIG. 13 includes diagrams illustrating the example of ACL reconstruction.

MODE FOR CARRYING OUT THE INVENTION

Hereinafter, exemplary embodiments of the present invention will be described, in detail with reference to the drawings. However, components described in the below embodiments are mere exemplary ones, and are nor intended to limit the technical scope of the present invention only to them.

First Embodiment

Before describing a drill bit, which is a first embodiment of a cutting instrument according to the present invention, knee ligament reconstruction will be described below as an example of usage of such a drill bit. However, the present invention is applicable not only to such knee ligament reconstruction but also to various situations of drilling a hole. In other words, the present invention can be used for drilling a hole in not only a bone, but also a solid body formed of any of various materials such as wood or metal.

Overview of Knee Ligament Reconstruction

When an anterior cruciate ligament (ACL) or a posterior cruciate ligament (PCL) is ruptured and unrepairable, in general, a treatment involving transplantation of a graft of tissue (i.e., ACL reconstruction or PCL reconstruction) is conducted. Because of its improved performance of surgery and early recovery in rehabilitation, ACL reconstruction is a surgical operation that is most frequently conducted among knee joint surgical operations. The surgical method has drastically advanced in the recent ten years, enabling a surgical operation to be performed via a small cut using an arthroscope.

Figure 17:
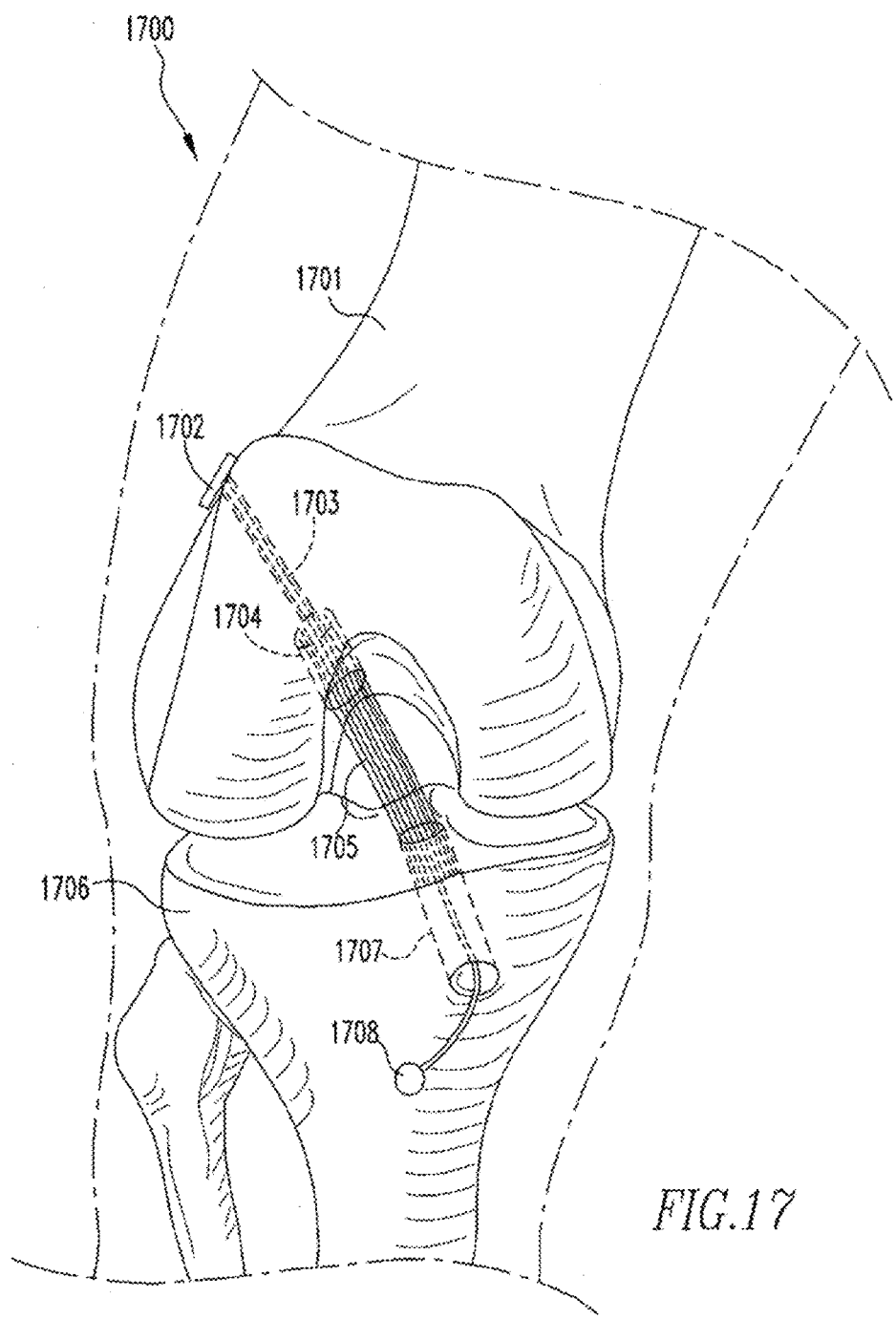
FIG. 17 is a diagram illustrating an example of ACL reconstruction.
Figure 18:
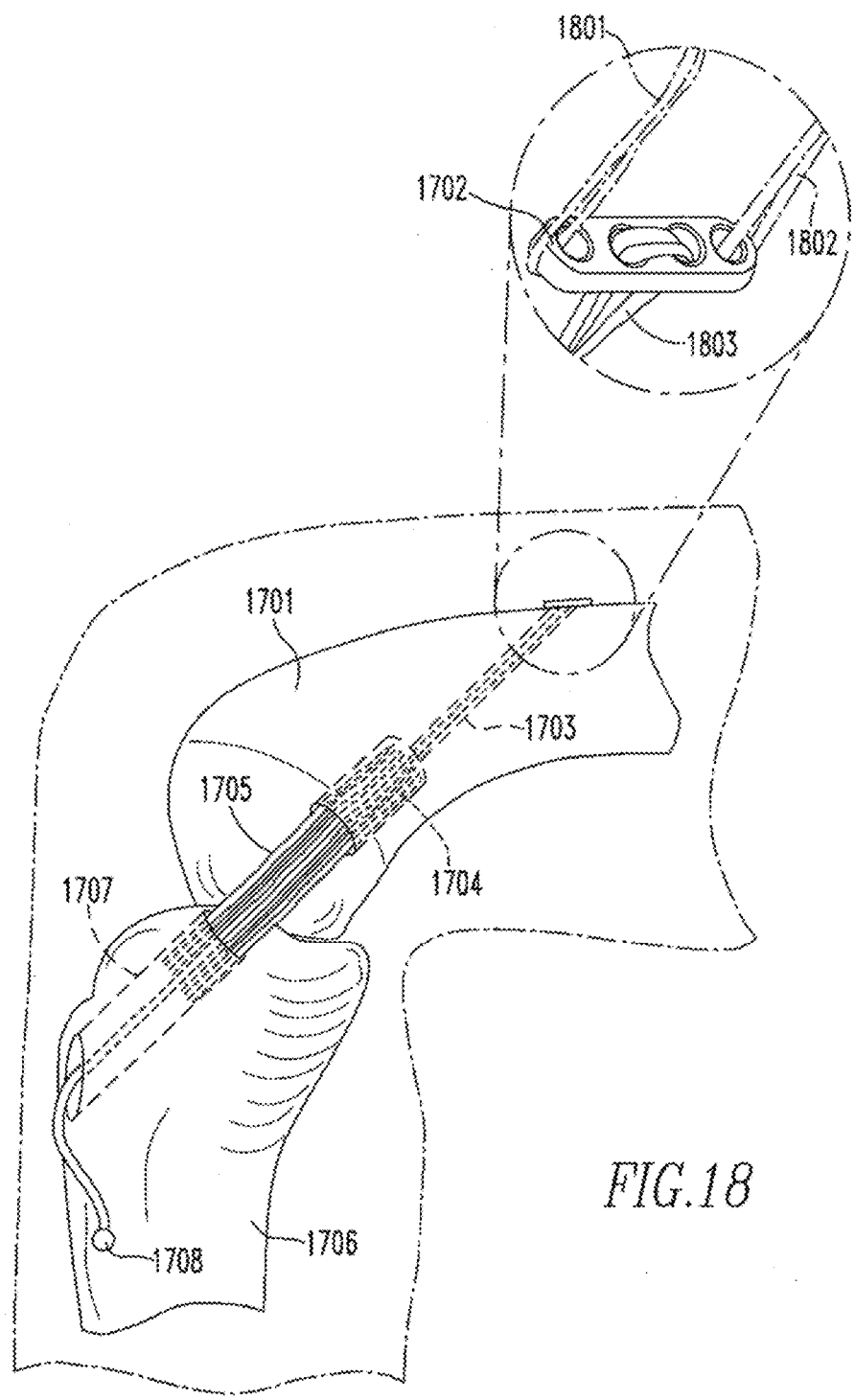
FIG. 18 is a diagram illustrating the example of ACL reconstruction.

FIGS. 17 and 18 are diagrams each illustrating an example of ACL reconstruction. FIG. 17 is a perspective diagram illustrating a femur 1701 and a tibia 1706 of a knee region 1700 of a right leg on the front side where the skin and muscles of the knee region 1700 are made transparent. Where an anterior cruciate ligament connecting the femur 1701 and the tibia 1706 is ruptured, bone holes 1704 and 1707 are formed in the femur 1701 and the tibia 1706, respectively, and a tendon transplant (graft) 1705 is inserted into the bone holes and fixed, thereby reproducing a function of an anterior cruciate ligament.

In general, the tendon transplant 1705 is obtained from, e.g., a part of a patellar tendon, and a semitendinous muscle and gracilis muscle, but may be formed from a synthetic material or a mixture of a synthetic material and a natural material. An end of the tendon transplant 1705 is inserted into the bone bole 1704 formed in the femur 1701, and another end thereof is inserted into the bone hole 1707 formed in the tibia 1706. Each end of the tendon transplant 1705 is attached to an endobutton 1702, or a fixture such as an interference screw 1708, and the fixture is fixed to a bone.

A method for using an endobutton 1702 will be described with reference to FIG. 19. As illustrated in a diagram 1901 in FIG. 19, a bone hole 1704 having a relatively large diameter ($\varphi$ 5 to $\varphi$ 10 mm) for inserting a tendon transplant 1705 therein is formed in a femur 1701. The diameter (thickness) of the tendon transplant is measured in advance, and a bone hole with a diameter corresponding (equal) to that size is created. Furthermore, where an endobutton 1702 (with a width of 4 mm) is used, a bone hole 1703 having a small diameter ($\varphi$ 4.5 mm) for allowing a thread 1803 extending from the tendon transplant 1705 to the endobutton and the endobutton 1702 to pass therethrough. If the bone hole 1704 is excessively lager relative to the tendon transplant 1705, poor adherence between the bone and the tendon transplant occurs sifter the surgical operation, and thus, ordinarily, a bone hole for insertion of a tendon transplant is provided with a small diameter. Where a bone hole is formed from the inside of a joint, a bone hole having a length of a sum of a length of a femur tendon transplant to be inserted (ordinarily, 15 to 20 mm) and a length of 6 mm required for turning the endobutton is created. Next, two threads 1801 and 1802 fastened to the endobutton 1702 are brought to the outside of the body from a subcutaneous tissue via the bone hole 1703 of the femur 1701.

Then, the endobutton 1702 is moved from the inside of the joint to the subcutaneous tissue via the bone holes 1704 and 1703 by mainly pulling the thread 1801.

Figure 19:
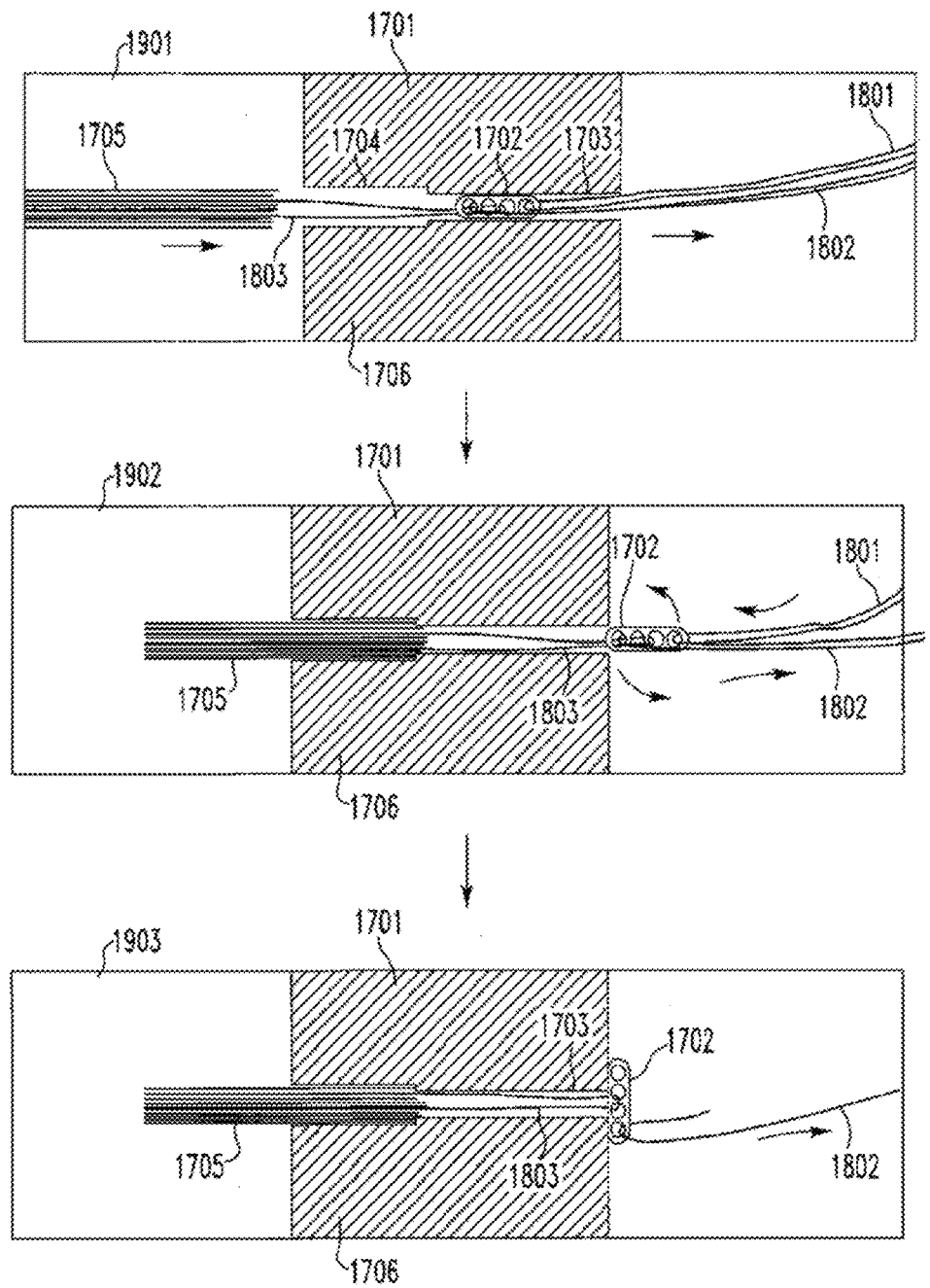

As illustrated in a diagram 1302 in FIG. 19, when the entire endobutton 1702 is brought out to the subcutaneous tissue, at that point of time, conversely, the thread 1801 is loosened while the thread 1802 is pulled. Consequently, the endobutton 1702 turns immediately outside the femur 1701.

As illustrated in a diagram 1903 in FIG. 19, where the endobutton 1702 turns by 90 degrees, the endobutton 1702 is caught by an exit of the bone hole 1703, and does not return to the inside of the femur 1701, and at that point of time, the tendon transplant 1705 is fixed. Lastly, the threads

1801 and 1802 are taken out of the endobutton 1702, whereby attachment of the tendon transplant 1705 to the femur 1701 side is completed.

For the tendon transplant 1705, a hamstring (tendon behind a knee) and a patellar ligament (ligament connecting a knee cap and a tibia) are used. FIGS. 17 and 18 illustrate a method in which one hole is created in a femur and one hole is created in a tibia, and a tendon is passed through the holes and fixed. However, recently, it has turned out that an anterior cruciate ligament is divided into two fibers, and thus, a method for reconstructing these two fibers (double bundle ACL reconstruction method) has been employed (Muneta 1999 and Yasuda 2006). In recent, years, there are an increased number of reports that the double bundle ACL reconstruction method, is more effective than the single bundle method in terms of recovery from anterior and rotary instability. In this double bundle ACL reconstruction method, a long tendon transplant is prepared using a hamstring, and two holes are created in a femur and two or three holes are created in a tibia to fix the tendon transplant therein (Anatomic Double Bundle ACL Reconstruction: Charles Crawford, John Nyland Sarah Landes, Richard Jackson, Haw Chong Chang, Akbar Hawab, David N. M, Caborn: Knee Surg Sports Traumatol Arthrosc (2007) 15, 946-9645.

Figure 20:
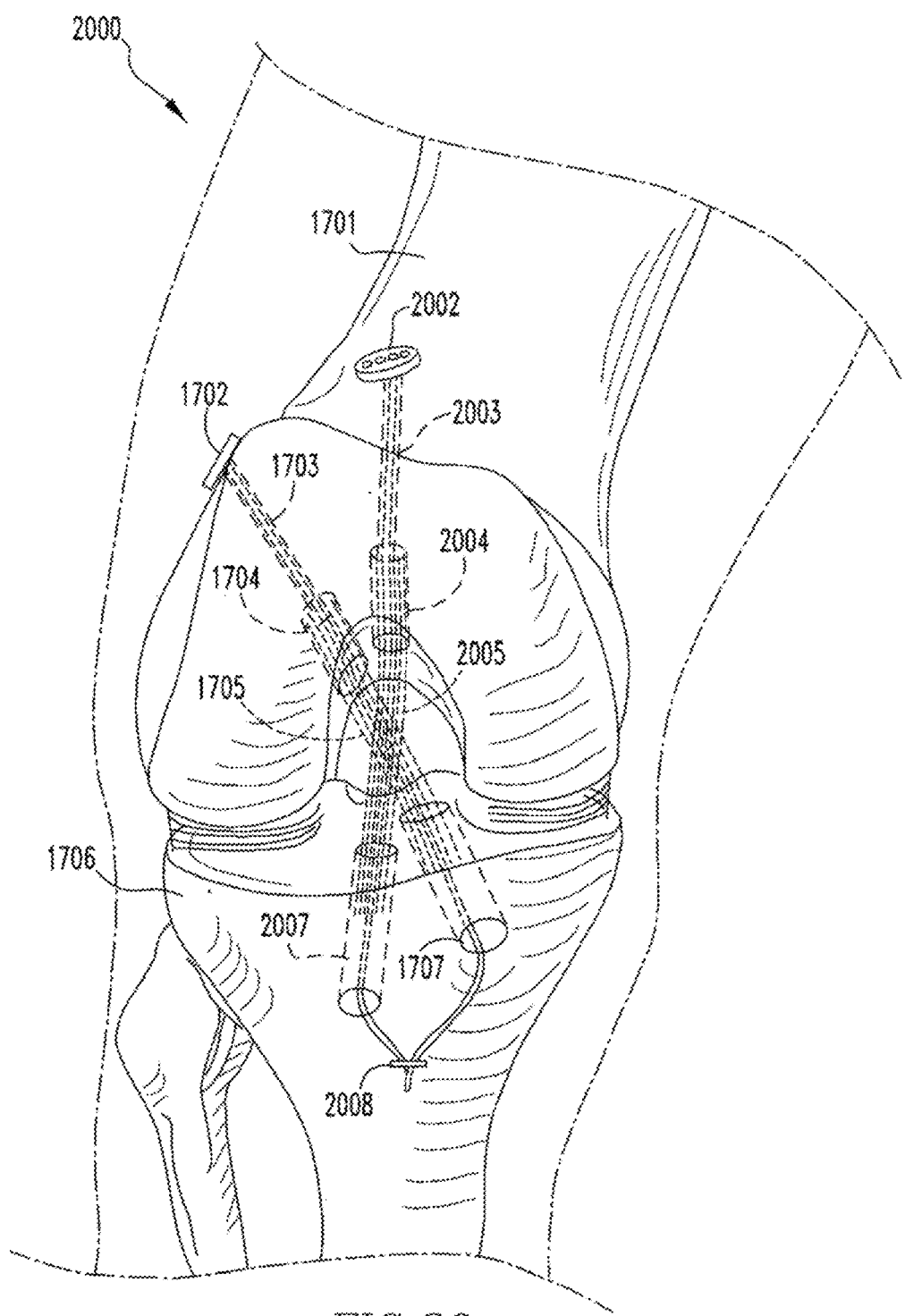
FIG. 20 is a diagram illustrating another example of ACL reconstruction.

FIG. 20 illustrates a knee region 2000 after tendon transplantation according to the double bundle ACL reconstruction method. In FIG. 20, two tendon transplants, i.e., anteromedial band (AM band) 2005 and a posterolateral band (PL band) 1705 are reconstructed. The double bundle ACL reconstruction method requires drilling bone holes 1703, 1704 and 1707 for the PL band 1705 and drilling bone holes 2003, 2004 and 2007 for the AM band 2005. Then, rising the two endobuttons 1702 and 2002, the PL band 1705 and the AM band 2005 are fixed. FIG. 20 illustrates a case where the PL band 1705 and the AM band 2005 are collectively fixed using a staple 2008 as a fixture on the tibia 1706 side.

As described above, in a knee ligament reconstruction surgical operation, it is said that a position where a tendon transplant is attached and the diameter of the tendon transplant are most important for the patient's early recovery and restoration close to a state before the tendon rupture. In other words, this definitely means that the positions, directions and sizes of the bone holes are important.

Although in FIG. 17, the bone hole 1707 formed in the tibia 1706 and the bone hole 1704 formed in the femur 1701 are substantially coaxially formed, in reality, there may be cases where the linear attachment of the tendon transplant 1705 as illustrated in FIG. 17 is undesirable from a somatological point of view. In other words, there are various restrictions on a position where the bone hole 1704 is created and the direction in which the bone hole 1704 is drilled, and thus, it is difficult to correctly and properly drill the bone hole 1704 on the femur 1701 side, from the tibia 1706 side.

Therefore, in recent years, a method called "outside-in" in which a bone hole 1704 is formed by drilling from the outside of the femur 1701, not from the tibia 1706 side has been desired. However, since a very important quadriceps exists outside the femur 1701, a hole with a large diameter cannot be created. Meanwhile, a tendon transplant 1705 and a bone hole 1704 for inserting the tendon transplant 1705 therein need to each have a certain diameter, and thus, with a bone hole having an extremely small diameter, a tendon transplant 1705 cannot be reconstructed. In other words, with an ordinary method, co-axial continuous bone holes having different diameters (bulb socket-like bone hole) cannot be created. When an endobutton is used as a fixture, it is necessary to form a bone hole having a diameter (6 mm) that is half of the length of the endobutton, and thus, consequently, it is inevitable to make the tendon transplant itself thin, which may result in insufficiency in strength of the tendon transplant.

Figure 16:
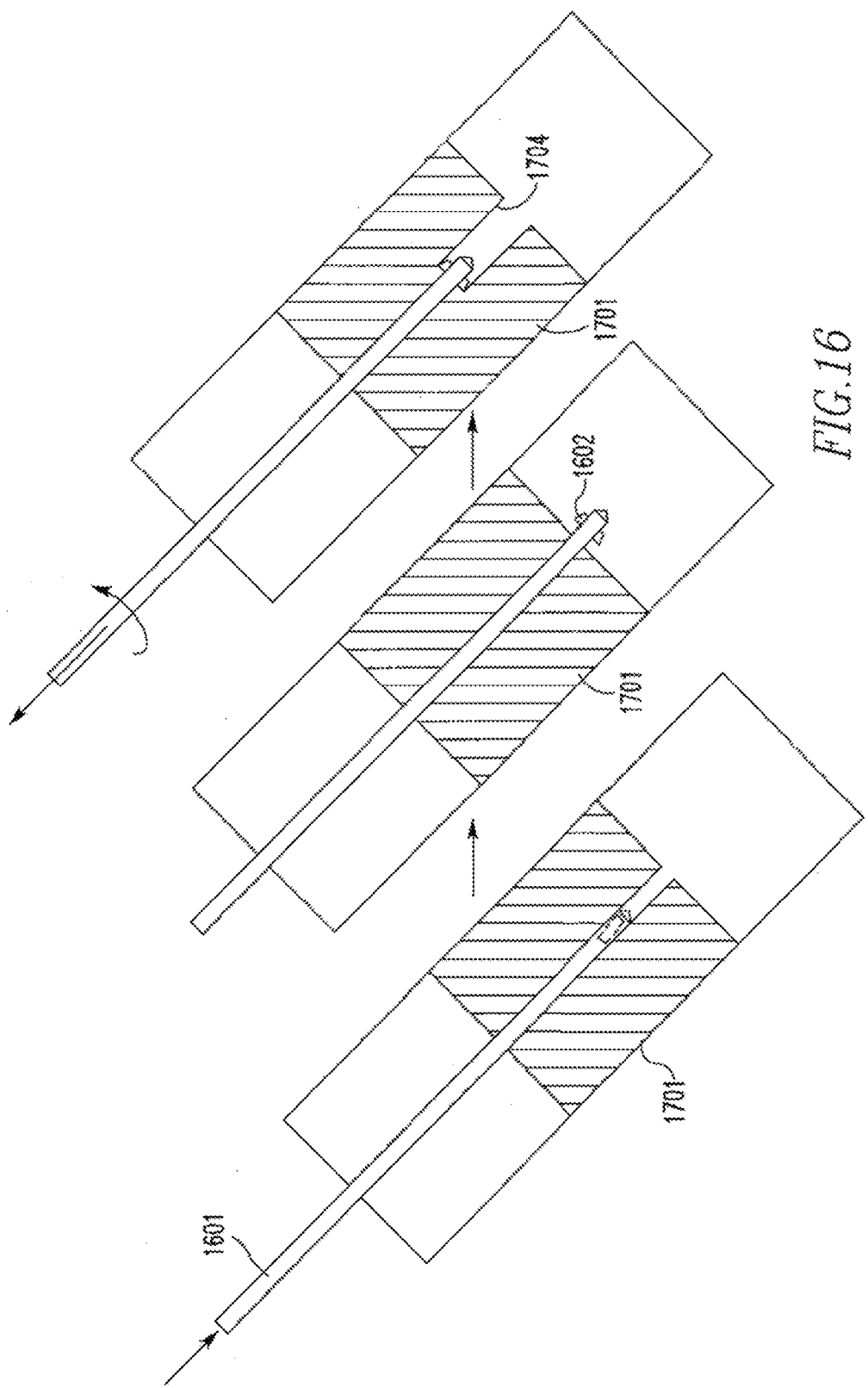
FIG. 16 includes diagrams illustrating a method for bone drilling in ACL reconstruction.

From the aforementioned facts, as illustrated in FIG. 16, a surgical method in which after drilling a hole from the outside of a femur 1701 using a drill bit 1601 with a small diameter, the same drill bit 1601 is kept inserted therein or another drill having a diameter that is substantially the same as that of the drill bit 1601 is inserted, and a blade 1602 is brought oat inside a joint, and a bone hole 1704 having a large diameter is formed, in an inner surface of the femur 1701 while the blade 1602 is pulled toward an operator has been desired.

A cutting instrument, which is a first embodiment of the present invention, is a drill bit used in such a surgical method.

Configuration of Drill Bit

Figure 1:
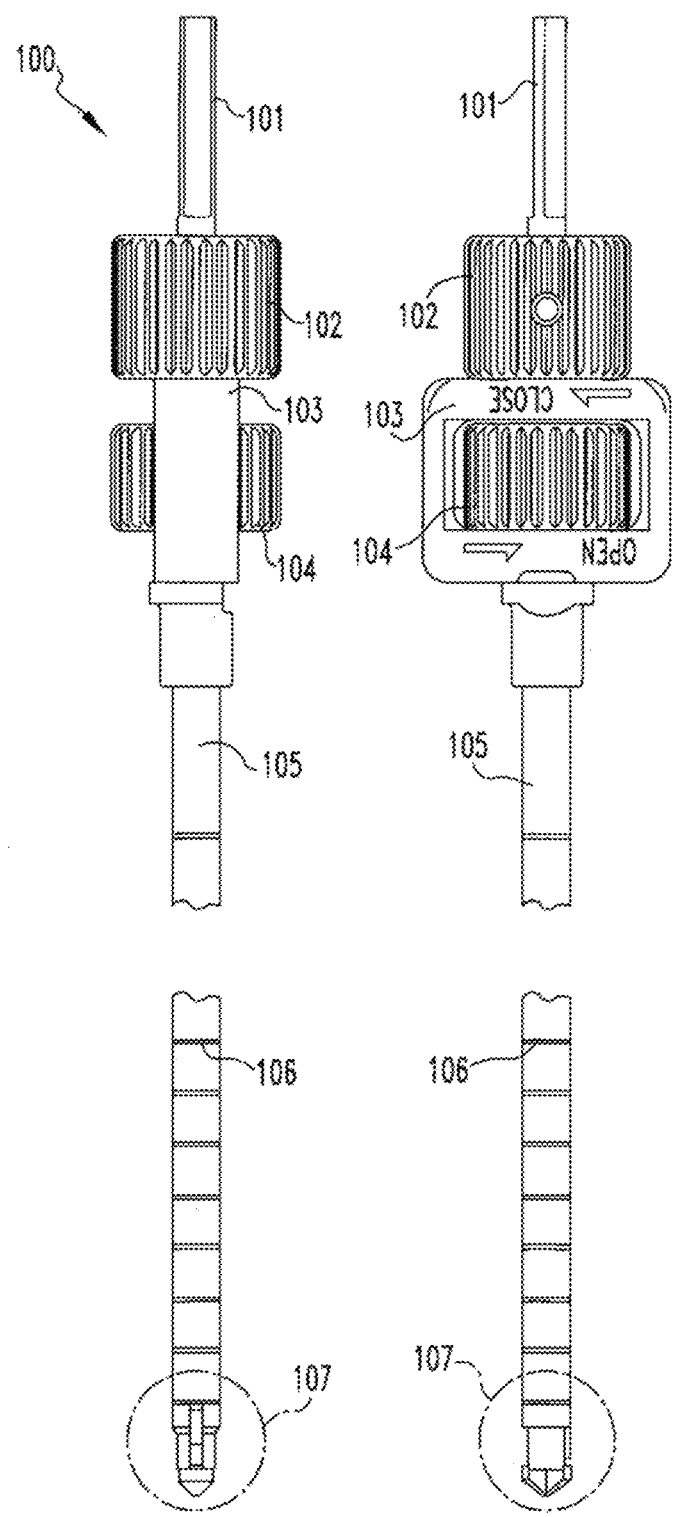
FIG. 1 includes diagrams each illustrating an overall configuration of a cutting instrument according to a first embodiment of the present invention.

FIG. 1 is a diagram illustrating an overall appearance of a drill bit 100 according to the present embodiment. The left-hand diagram is a front view and the right-hand diagram is a right-side view. A drill bit 100 includes an elongated member including a tubular portion 105 and a shaft-like portion 101 inserted in the tubular portion 105. An upper portion of the shaft-like portion 101 in the FIG. is chucked to a non-illustrated drill motor and rotated, whereby cutting is performed at a distal end portion 107 of the drill bit 100.

A grip 102 is fixed, to the shaft-like portion 101 and formed integrally with the frame-like portion 103. The frame-like portion 103 has a hollow angular tubular shape, and receives a rotational operation portion 104 inside. The rotational operation portion 104 is provided so as to be rotatable relative to the shaft-like portion 101 and the frame-like portion 103. An inner portion of the rotational operation portion 104 is threaded, and the tubular portion 105 engages with the thread. By rotating the rotational operation portion 104, the tubular portion 105 moves in an axial direction thereof relative to the shaft-like portion 101. Here, a state in which the tubular portion 105 has been moved to a position closest to the hands of an operator (upper side in Figure) as a result of rotating the rotational operation portion 104 in a closing direction (left-hand direction in the Figure). In other words, the rotational operation portion 104, etc., function as an operation portion provided at another end of the elongated member, the operation portion moving the shaft-like portion 101 and the tubular portion 105 relative to each other.

On an outer peripheral surface of the tubular portion 105, marks 106 are provided at regular intervals. From the positions of the marks 106, the amount of the drill bit 100 inserted and the amount of the drill bit 100 pulled out after the insertion can be recognized. It is desirable that the drill bit 100 have a total length of approximately 300 mm and, the tubular portion 105 have an outer diameter of 4.5 mm. This is because such sires enable a bone hole having a diameter suitable for insertion of an endobutton to be formed in a femur.

Figure 2:
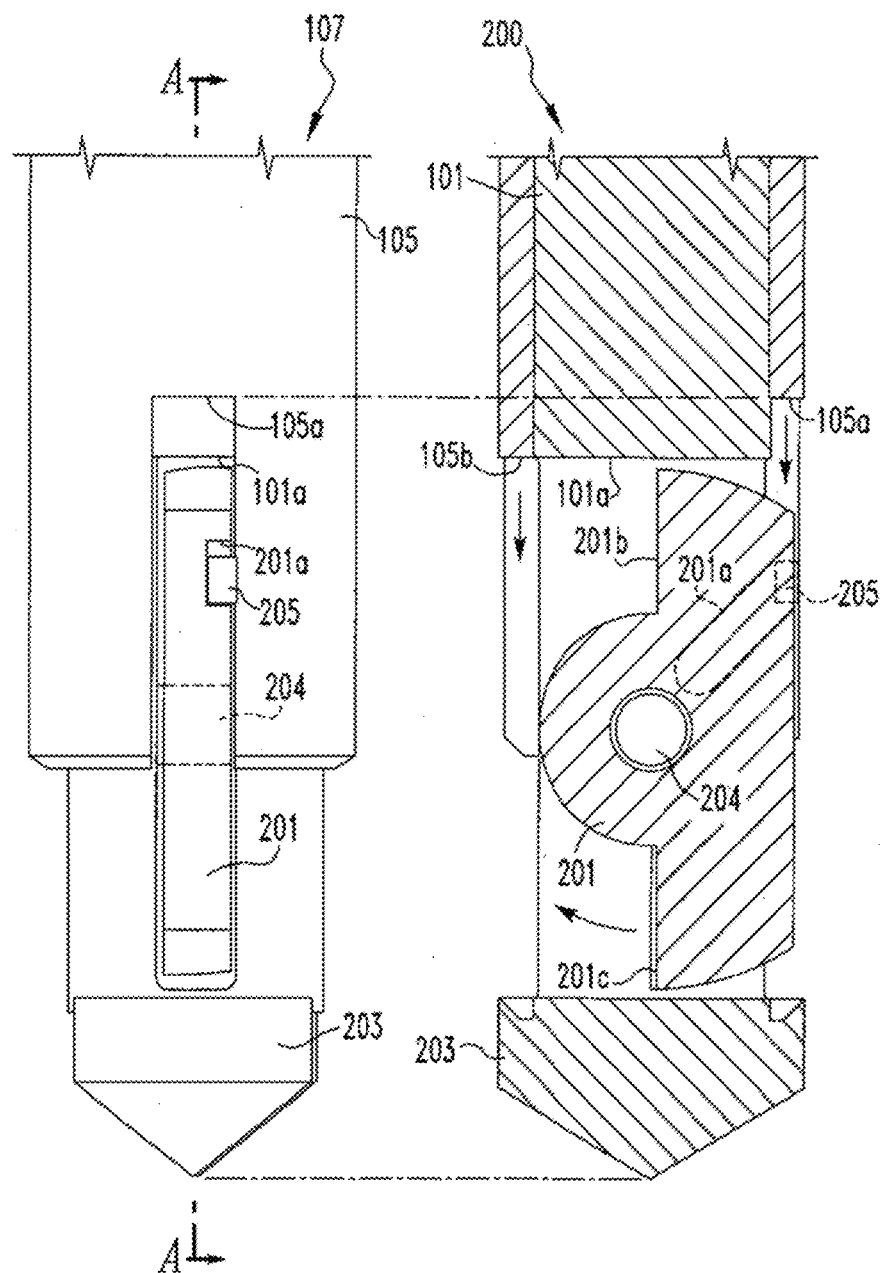
FIG. 2 includes diagrams each illustrating a distal end configuration of the cutting instrument according to the first embodiment of the present invention.

FIG. 2 includes enlarged diagrams in which a distal end portion 107 of the drill bit 100 has been enlarged. The left-hand diagram is an enlarged side view and the right-hand diagram is a cross-sectional view thereof taken along line A-A. At an end portion of the shaft-like portion 101, a distal end cutter 203 is formed, and at a position closer to an operator relative to the distal end cutter 203, a slit 101*a* is provided. The slit 101*a* is an angular hole having a width smaller than an outer diameter of the shaft-like portion 101, and in a center portion thereof, a pin 204 is inserted. A blade 201 that includes two edges 201b and 201c and is rotatable about the pin 204 is attached to the pin 204. At a surface of the blade 201, a groove portion 201a is formed, providing a mechanism in which a protruded portion 205, which is a part of the tubular portion 105, moves within the groove portion 201a. Upon the tubular portion 105 moving downward in the Figure, the protruded portion 205 makes the blade 201 pivot about the pin 204 while advancing within the groove portion 201a. The protruded portion 205 and the groove portion 201a function as a motion mechanism that converts a relative movement of the shaft-like portion 101 and the tubular portion 105 resulting from an operation of the rotational operation portion 104 to a pivoting of the blade 201 between a housed position and a projected position. In other words, in the motion mechanism, the protruded portion 205 of the tubular portion 105 moves vertically and linearly, thereby a pressing force being imposed on an inner wall surface of the groove portion 201a, and the pressing force produces a turning force that turns the blade 201. In other words, the protruded portion 205 provides a turning force no the blade while moving within the groove portion 201a.

Consequently, the two edges 201b and 201c of the blade 201 move so as to project from silts 105a and 105b formed at a distal end of the tubular portion 105 to the outside of the tubular portion 105. In other words, the blade 201 is pivotable between a housed position where the blade 201 is housed in the elongated member of the drill bit, and a projected position where the edges 201b and 201c are projected outside the elongated member.

Figure 3:
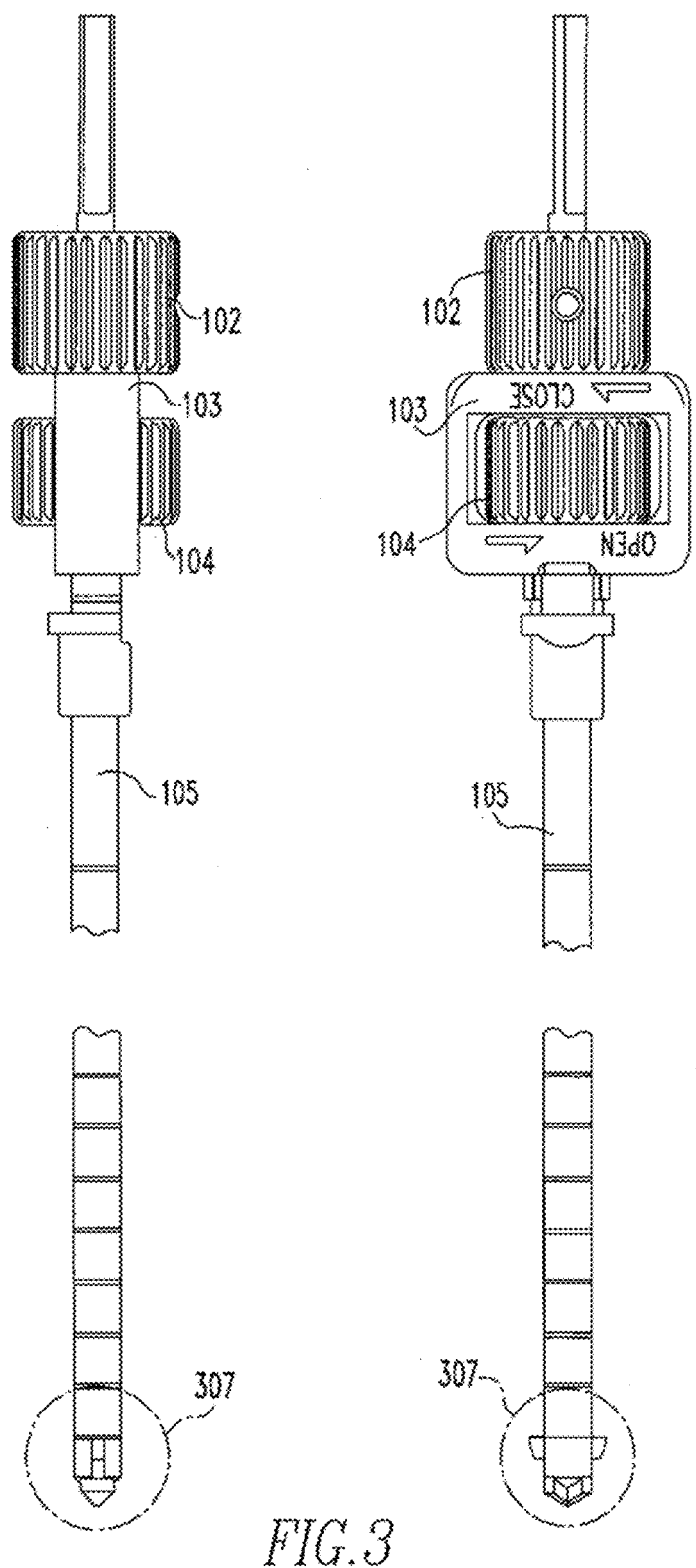
FIG. 3 includes diagrams each illustrating an overall configuration of the cutting instrument according to the first embodiment of the present invention.

FIG. 3 includes diagrams each illustrating an outer appearance of the drill bit 100 when the blade 201 is brought out at the distal end portion 10 in FIG. 1. As in FIG. 1, the left-hand diagram is a side view and the right-band diagram is a front view. As illustrated in FIG. 3, the blade 201 is projected on sides in the distal end portion 307. In such state, the entire drill bit 100 is pulled back in the upward direction in the Figure while being rotated, enabling formation of a bone hole 1704 having a large diameter such as those illustrated in, e.g., FIGS. 16 and 20.

Figure 4:
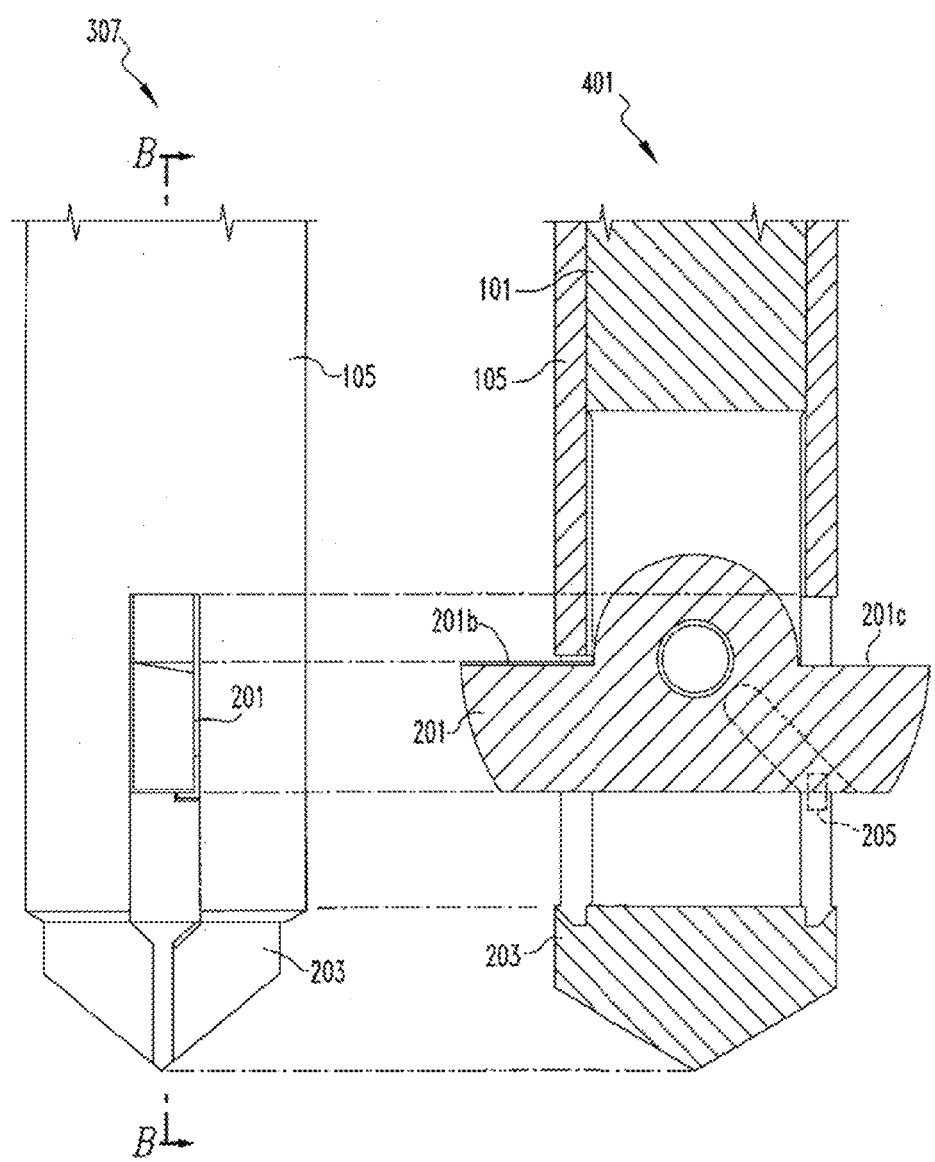
FIG. 4 includes diagrams each illustrating a distal end configuration of the cutting instrument according to the first embodiment of the present invention.

FIG. 4 includes diagrams in which the distal end portion 307 in FIG. 3 has been enlarged: the left-hand one is a side view and the right-hand one is a cross-sectional diagram thereof taken along line B-B, As illustrated in FIG. 4, the tubular portion 105 moves downward relative to the shaft-like portion 101, whereby the blade 201 receives a force of the protruded portion 205 and makes a right-hand, turn in the Figure, and consequently, the edges 201b and 201c are stuck out of the tubular portion 105. The edges 201b and 201c are arranged in a direction perpendicular to an axis of the shaft-like portion 101.

Figure 6:
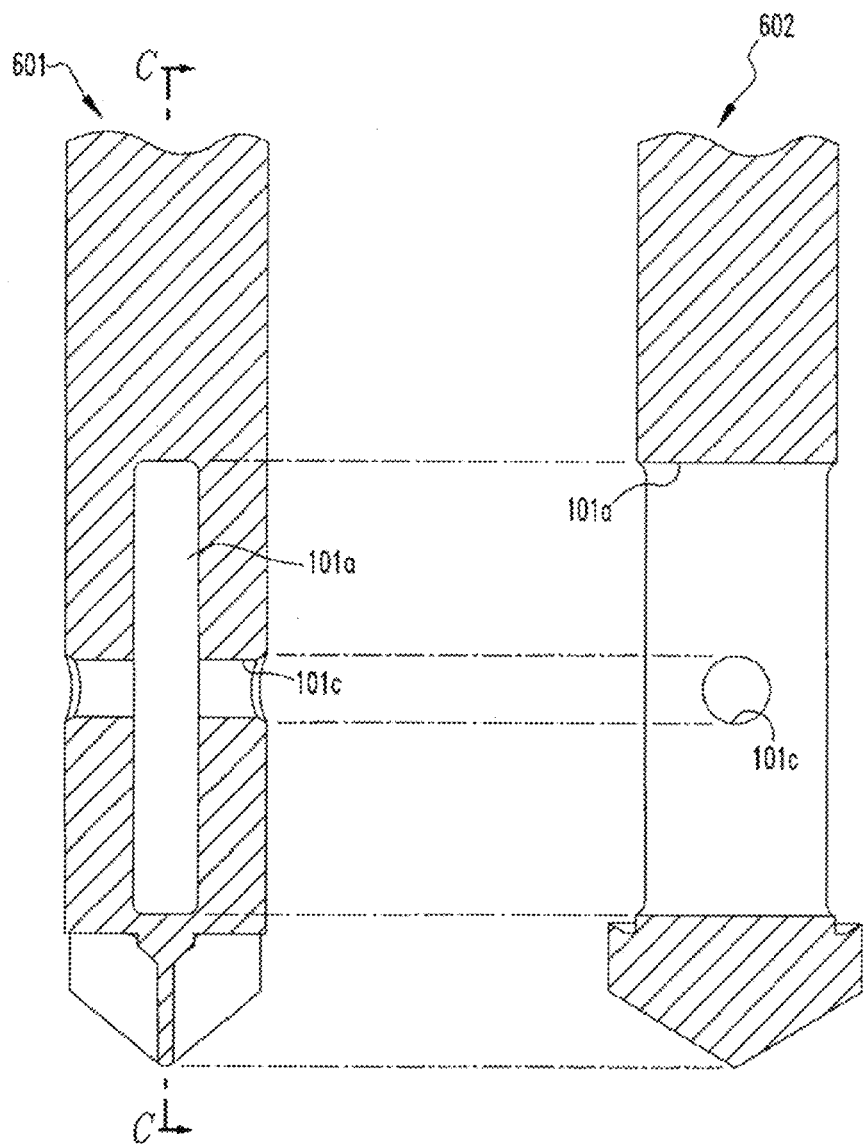
FIG. 6 includes diagrams each illustrating a distal end configuration of the shaft-like portion according to the first embodiment of the present invention.
Figure 7:
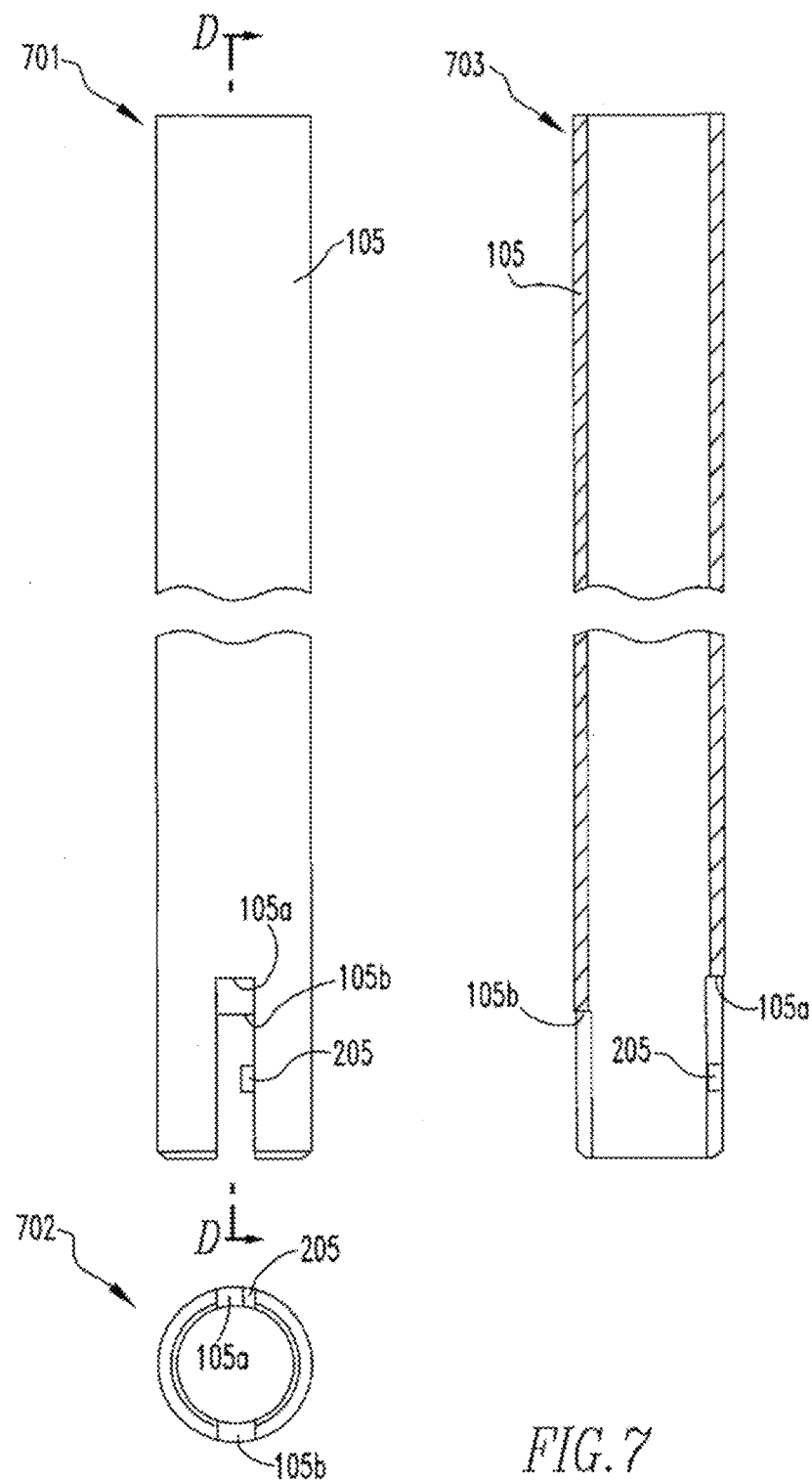
FIG. 7 includes diagrams each illustrating a distal end configuration of a tubular portion according to the first embodiment of the present invention.
Figure 8:
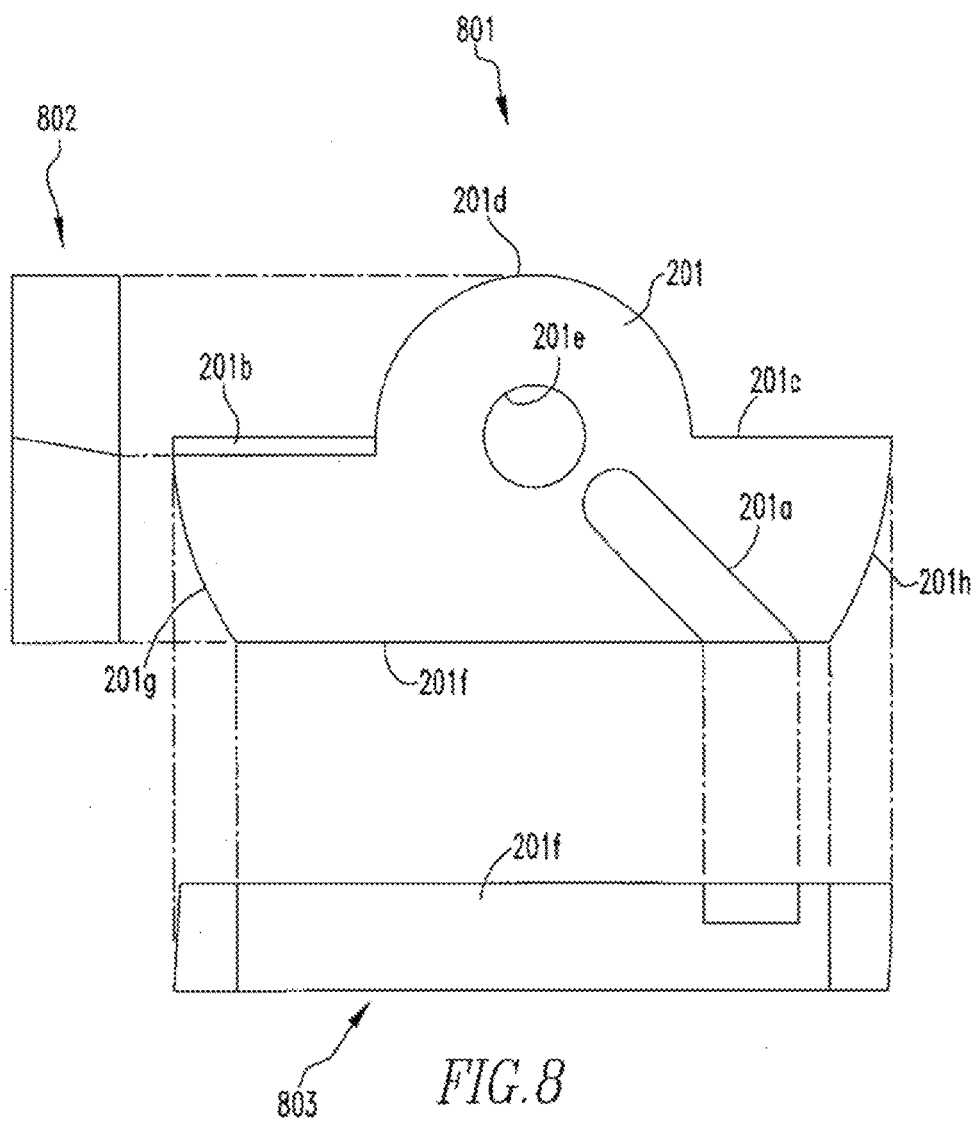
FIG. 8 includes diagrams each illustrating a configuration of a blade according to the first embodiment of the present invention.

FIGS. 5 to 8 are diagrams each illustrating a component of the drill bit 100 when the drill bit 100 is disassembled: FIG. 5 illustrates the shaft-like portion 101, FIG. 6 illustrates a distal end of the shaft-like portion 101, FIG. 7 illustrates the tubular portion 105, and FIG. 8 illustrates the blade 201.

FIG. 5 includes a front view (501), an enlarged plan view (502), an enlarged bottom view (503) and a right-side view (504) of the shaft-like portion 101. As illustrated in the front view (501), an end of the shaft-like portion 101 includes a chuck portion 101b to be attached to the non-illustrated drill motor. Then, as has already been described with reference to FIG. 2, at another end of the shaft-like portion 101, the distal end cutter 203 and the slit 101a are formed. Furthermore, as illustrated in the right-side view (504), at a side surface of the distal end of the shaft-like portion 101, a through hole 101c for allowing the pin 204, which is a turning axis of the blade 201, to be fitted therein is formed.

FIG. 6 illustrates an enlargement of a distal end portion 507 of the shaft-like portion 101 illustrated in FIG. 5. FIG. 6 includes a cross-sectional diagram (601) illustrating an inner portion of the enlarged distal end portion and a cross-sectional diagram (602) thereof taken along line C-C. As illustrated in FIG. 6, the slit 101a and the through hole 101c intersect each other in the inner portion of the shaft-like portion 101, The slit 101a is formed so as to have a size depending on the size or the blade 201 to be inserted therein.

FIG. 7 includes a front view diagram (701) and a bottom view diagram (702) of the tubular portion 105 and a cross-sectional diagram (703) thereof taken along line D-D. As illustrated in these diagrams, the tubular portion 105 includes the mutually facing slits 105a and 105b at the distal end thereof. The slit 105a is formed so as to have a width that is the same as that of the slit 105b and be longer than the slit 105b so that the blade 201 can vertically be housed. At a position somewhat below a center part of the slit 105a, the protruded portion 205 is provided. The protruded portion 205 can be formed, for example, simultaneously with cutting the tubular portion 105 to form the slit 105a.

FIG. 3 includes a front view diagram (801), a left-side view diagram (802) and a bottom view diagram (803) of the blade 201. As illustrated in these diagrams, the blade 201 has a shape in which the two edges 201b and 201c are connected via a circular arc portion 201d. At a center portion of the circular arc portion 201d, a through hole 201e for allowing the pin 204, which is a turning axis, to be loosely inserted therein. A bottom portion 201f is formed so as to be planar, and at a position somewhat inward of an end of the bottom portion 201f, an exit of the groove portion 201a is provided. The groove portion 201a is linearly provided from the exit toward the through hole 201e, and is formed so as to have a width allowing the protruded portion 205 of the tubular portion 105 to be inserted therein. Side portions 201g and 201h connecting the edges 201b and 201c, and the bottom portion 201f, of the blade 201 are each formed so as to have a curved surface so that the blade 201 does not interfere with the tubular portion 105 when turning about the pin 204.

Figure 9:
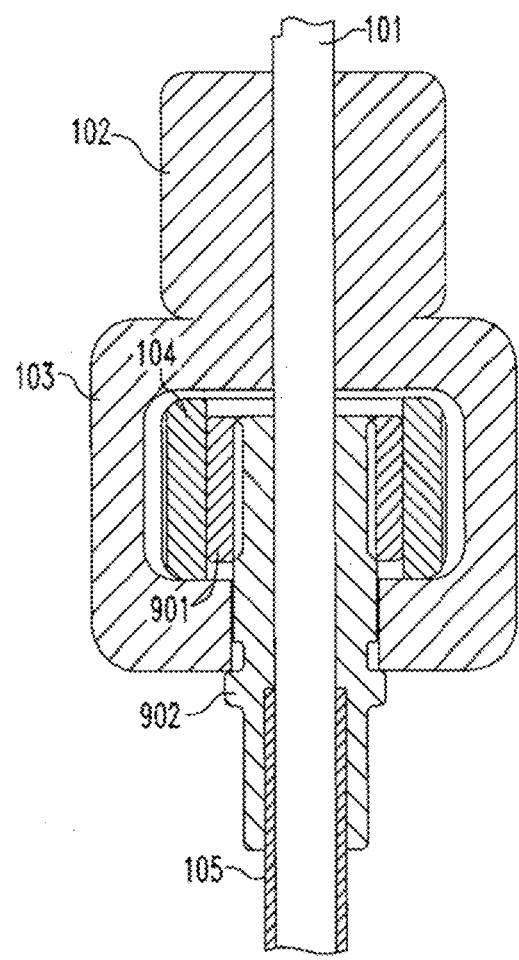
FIG. 9 is a diagram illustrating a configuration of an operation portion of the cutting instrument according to the first embodiment of the present invention.

FIG. 9 is an enlarged cross-sectional diagram of a handle portion of the drill bit 100 illustrated in FIG. 1. The grip 102 is fixed to the shaft-like portion 101 and is formed integrally with the frame-like portion 103. The frame-like portion 103 has a hollow angular tubular shape, and houses the rotational operation portion 104 inside. The rotational operation portion 104 is provided so as to be rotatable relative to the shaft-like portion 101 and the frame-like portion 103. A threaded block nut 901 is fitted in the inner portion of the rotational operation portion 104, and a guide portion 902 fixed to the outside of the tubular portion 105 engages with the thread. By rotating the rotational operation portion 104, a force in the axial direction is transmitted to the guide portion 902 via the block nut 901, whereby the tubular portion 105 moves relative to the shaft-like portion 101 in the axial direction.

The drill bit 100 configured as described above has a mechanism in which edges project on opposite sides of the tubular portion 105, enabling a double increase of the cutting efficiency and a decrease in vibration during cutting. Furthermore, the drill bit 100 has a favorable balance of loads relative to one axis, and thus, is difficult, to break. In particular, where the drill bit 100 is used for drilling a hole in bone, while a vibration decrease is a very important issue, the vibration can substantially be decreased compared to a mechanism in which an edge projects only on one side of the tubular portion. Furthermore, wobbling of the axis is also reduced, and thus, a bone hole having a small diameter and a bone hole having a large diameter can accurately and coaxially be formed, enabling very smooth insertion of an endobutton.

Second Embodiment

Figure 10:
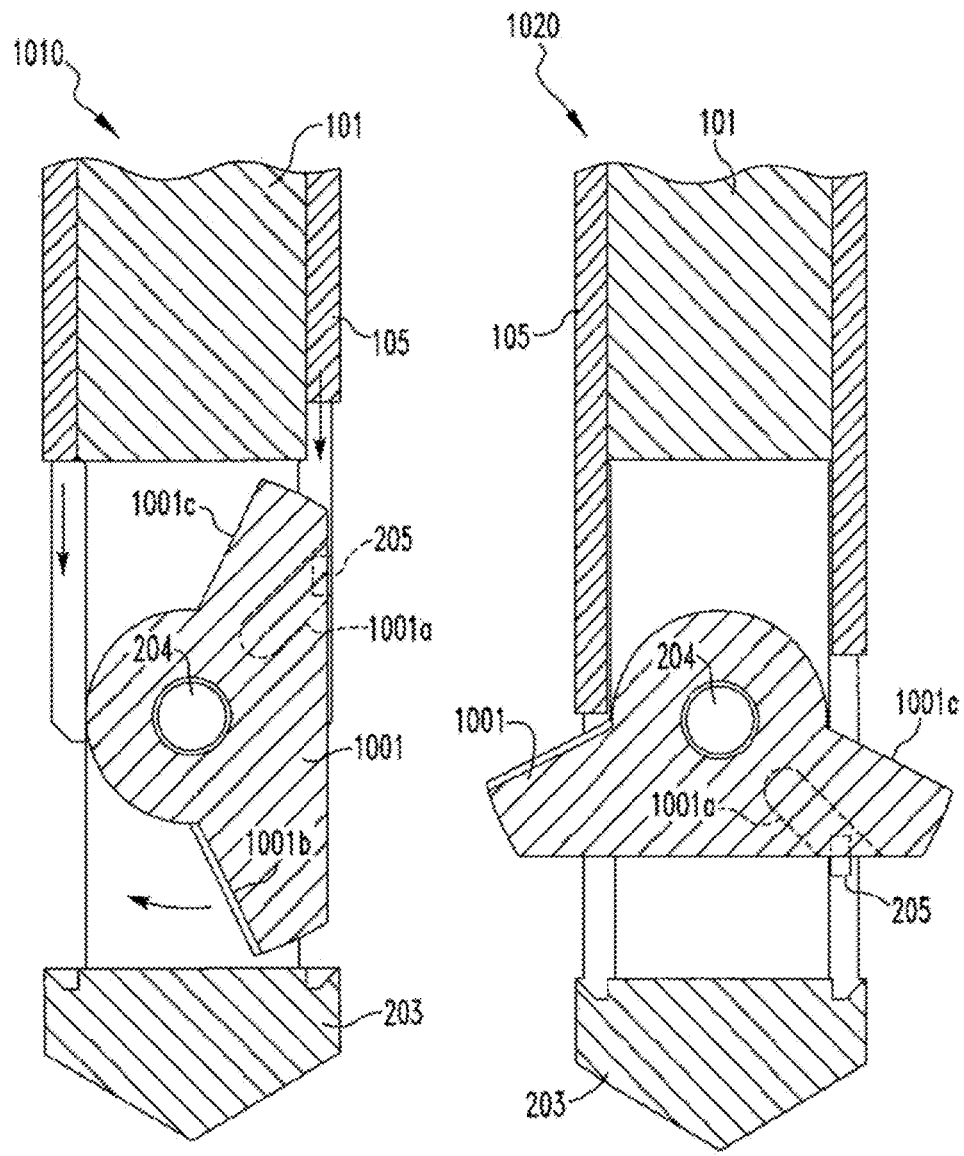
FIG. 10 includes diagrams each illustrating a configuration of a blade according to a second embodiment of the present invention.

A drill bit, which is a second embodiment of the present invention, will be described with reference to FIG. 10. FIG. 10 includes cross-sectional, diagrams (1010 and 1020) each illustrating a distal end portion of a drill bit according to the present embodiment, and the diagrams correspond to the cross-sectional diagrams (601 and 602) in FIG. 6. In the present embodiment, also, a blade 1001 includes a groove portion 1001a, and a protruded portion 205 moves within the groove portion 1001a, thereby the blade 1001 turns by 90 degrees relative to the tubular portion 105.

However, as opposed to the first embodiment, in the present embodiment, two edges 1001b and 1001c included in the blade 1001 are formed at an angle so as to form a shape projecting toward the hands of an operator, not forming a straight line perpendicular to the axis of the shaft-like portion 101. In other words, while in the first embodiment, center lines of edge surfaces of the edges 201b and 201c of the blade 201 lie on an identical straight line, in the present embodiment, center lines of edge surfaces of the two edges 1001b and 1001c intersect each other at an acute angle. In other words, the blade 1001 is a plate having a shape of a rough isosceles triangle in its entirety, and the edges are provided on the two oblique sides of the isosceles triangle. The remaining configuration and functions are similar to those of the first embodiment, and thus, a description thereof will be omitted here.

The present embodiment enables a decrease in resistance and vibration at the time of starting cutting. Furthermore, a bone hole having a large diameter can be formed, so as to taper, enabling a tendon transplant to be fitted more firmly. Furthermore, situations where an endobutton is hung up during insertion can be reduced.

Third Embodiment

Figure 11:
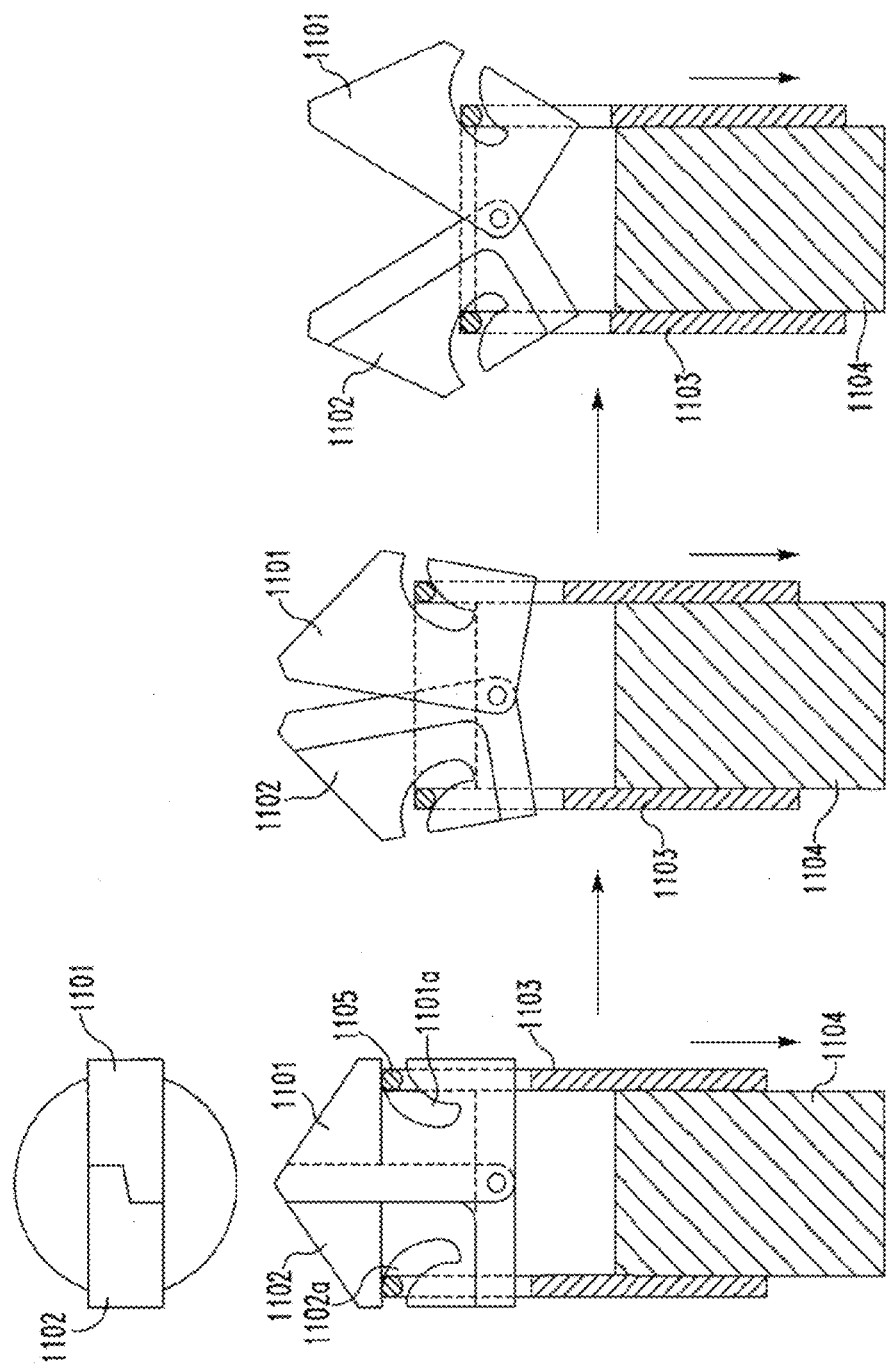
FIG. 11 includes diagrams each illustrating a configuration of a distal end portion according to a third embodiment of the present invention.
Figure 12:
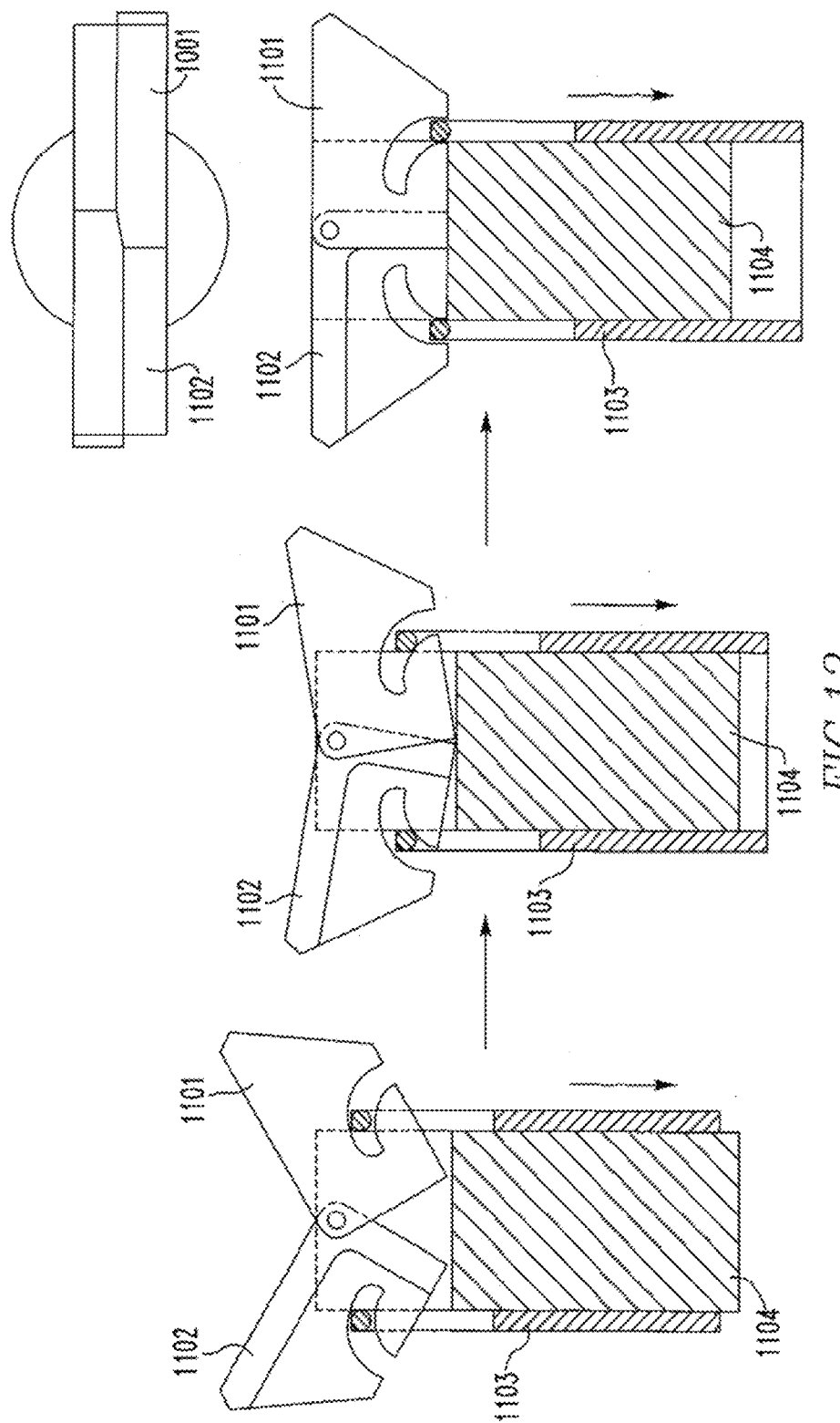
FIG. 12 includes diagrams each illustrating a configuration of the distal end portion according to the third embodiment of the present invention.

A drill bit, which is a third embodiment of the present invention, will be described with reference to FIGS. 11 and 12. FIG. 11 is a cross-sectional diagram illustrating changing of a distal end portion of a drill bit according to the present embodiment. As opposed to the first and second embodiments, the distal end of the drill bit includes two blade parts 1101 and 1102 pivotally supported by a shaft-like portion 1104. Then, a tubular portion 1103 moves relative to the shaft-like portion 1104, thereby the blade parts 1101 and 1102 being opened/closed. In other words, a blade includes a combination of two blade parts 1101 and 1102 each including one edge. The remaining configuration and functions are similar to those of the first embodiment, and thus, a description thereof will be omitted here.

In the left-hand diagram in FIG. 11, the blade parts 1101 and 1102 are in a closed state, and jointly form a distal end cutter. The drill bit is rotated in this state to advance upward in the Figure, enabling drilling a hole having a small diameter. The blade parts 1101 and 1102 each include a stepped end edge inside, which are fitted on each other and thereby integrated to function as a distal end cutter.

Meanwhile, the tubular portion 1103 is moved downward in the Figure relative to the shaft-like portion 1104 (toward an operator viewed from the operator), thereby the blade parts 1101 and 1102 start opening horizontally as illustrated in the center diagram. Protruded portions 1105 formed, at the tubular portion 1103 move within groove portions 1101a and 1102a of the blade parts 1101 and 1102, respectively, thereby proving a force in the rightward direction in the Figure to the blade part 1101, and a force in the leftward direction in the Figure to the blade part 1102. This point is similar to the first and second embodiments.

Furthermore, when the tubular portion 1103 is moved downward in the Figure relative to the shaft-like portion 1104, the blade parts 1101 and 1102 gradually open to enter the state illustrated in the right diagram in FIG. 11. Then, the blade parts 1101 and 1102 than change to the states in the left, center and right diagrams in FIG. 12. Lastly, as illustrated in the right diagram in FIG. 12, the blade parts 1101 and 1102 stick out on opposite sides of the tubular portion 1103. In this state, the drill bit is pulled toward the operator while being rotated, enabling holes having different sires to be drilled at one time as in the first and second embodiments.

According to the present embodiment, two blades function as a distal end cutter, enabling a space for opening/closing the blades to be small. In other words, if the present embodiment is used for knee ligament reconstruction, after formation of a bone hole having a small diameter, it is possible that the blades are extended with minimum insertion and a bone hole having a large diameter can be formed. In other words, the duration of surgery can substantially be reduced, and safer and less-invasive ligament reconstruction can be performed.

Fourth Embodiment

Figure 13:
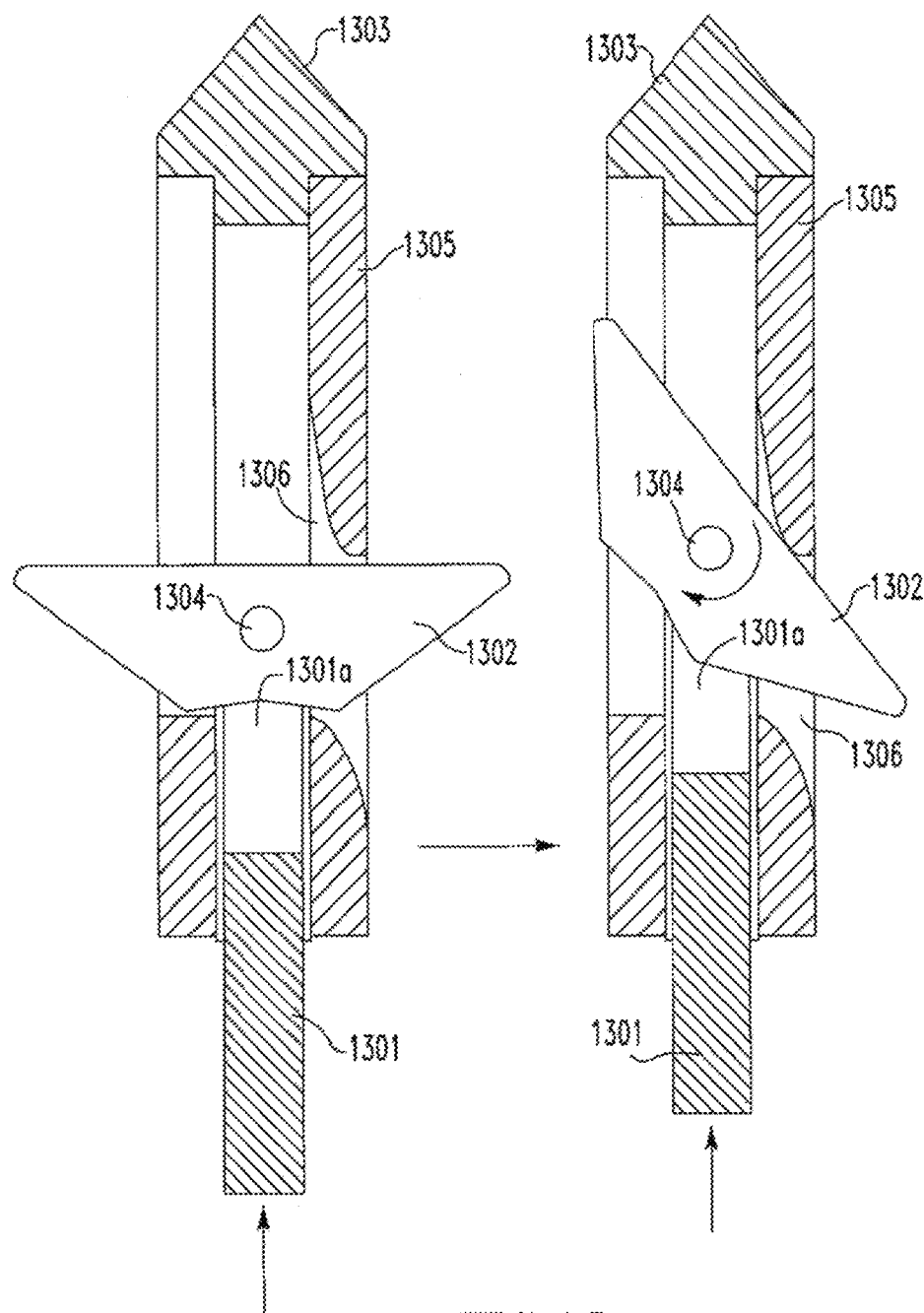
FIG. 13 includes diagrams each illustrating a configuration of a distal end portion according to a fourth embodiment of the present invention.
Figure 14:
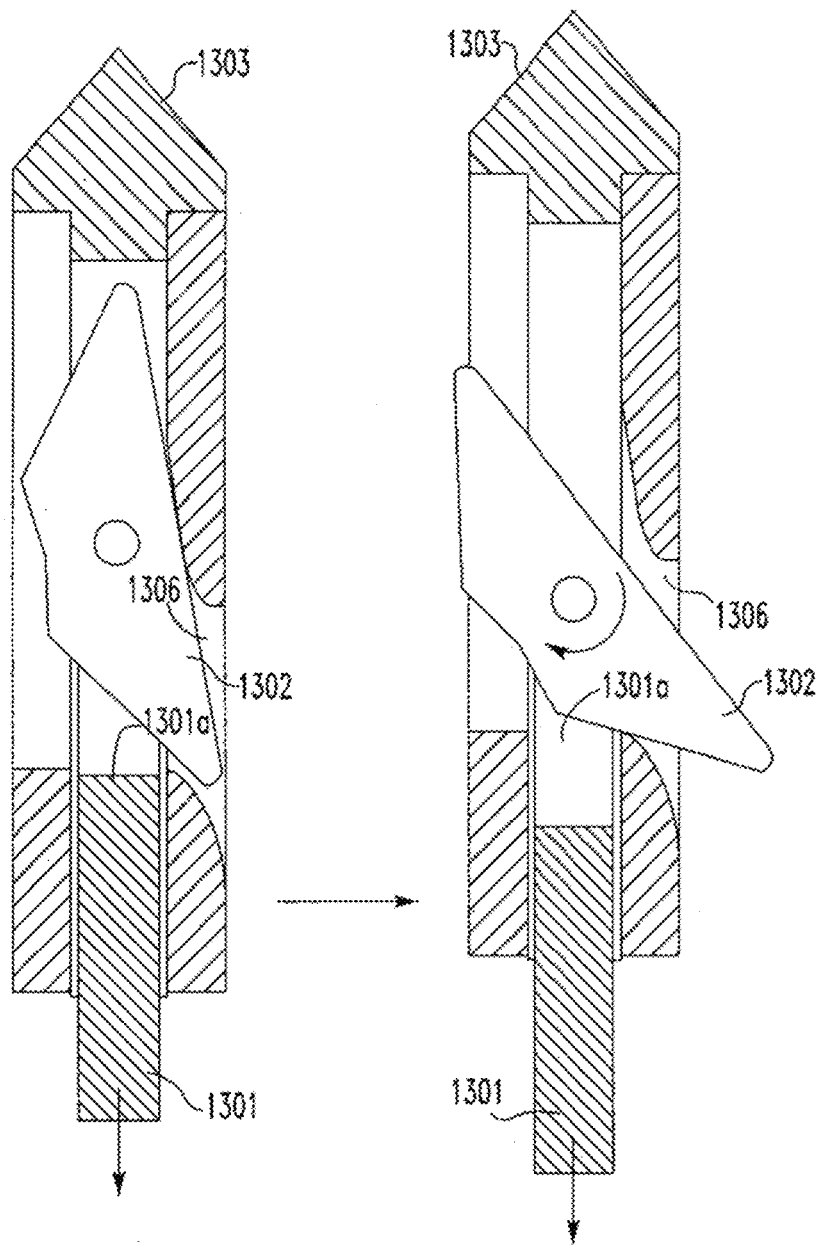
FIG. 14 includes diagrams each illustrating a configuration of the distal end portion according to the fourth embodiment of the present invention.

A drill bit, which is a fourth embodiment of the present invention, will be described with reference to FIGS. 13 and 14. FIGS. 13 and 14 are cross-sectional diagrams illustrating changing of a distal end portion of a drill bit according to the present embodiments FIG. 13 illustrates a state in which a blade 1302 is opened. FIG. 14 illustrates a state in which the blade 1302 is closed. In the first and second embodiments, the protruded portion 205 provided at the tubular portion 105 and the groove portions 201a and 1001a of the respective blade 201 and 1001 engage with each other, thereby opening/closing the blade 201. Meanwhile, in the present embodiment, an oblique surface (inner surface in an axial direction) of a slit 1306 provided, in the tubular portion 1305 abuts to an edge or a surface opposite to the edge (i.e., a part of an outer peripheral surface) of the blade 1302, whereby the blade 1302 turns, opening/closing edges. As opposed to the first to third embodiments, a shaft-like portion 1301 is moved, with the tubular portion 1305 fixed, thereby opening/closing the edges.

In FIG. 13, as in the first and second embodiments, the blade 1302 is pivotally supported by a pin 1304 fixed within a slit 1301a of the shaft-like portion 1301, and attached so that the blade 1302 can turn about the pin 1304. The shaft-like portion 1301 is moved upward in the Figure (toward the back viewed from an operator), whereby a surface of the slit 1306 formed at the tubular portion 1305, the surface being inclined to the distal end side toward an axis and the blade 1302 abut to each other, thereby a force that makes the blade 1302 has a right-hand turn in the Figure being imposed on the blade 1302. Consequently, the blade 1302 is housed as illustrated in the left diagram in FIG. 14. Meanwhile, the shaft-like portion 1301 is moved downward in the Figure (toward an operator viewed from the operator), enabling the blade 1302 to be projected outside the tubular portion 1305 as illustrated, in the right diagram in FIG. 14.

In this case, a lower inclined surface of the slit 1306 abuts to an edge of the blade 1302, whereby the blade 1302 turns. Meanwhile, in the present embodiment, the distal end cutter 1303 of the drill bit is fitted in and fixed to the tubular portion 1305.

The configuration of the present embodiment is effective for a case where a drill bit has a smaller outer diameter or a case where a strength of the protruded portion 205 illustrated in FIG. 2 cannot be ensured. The distal end cutter 1303 is fixed to the tubular portion 1305, and thus, a more strong drilling force can be exerted.

Fifth Embodiment

Figure 15:
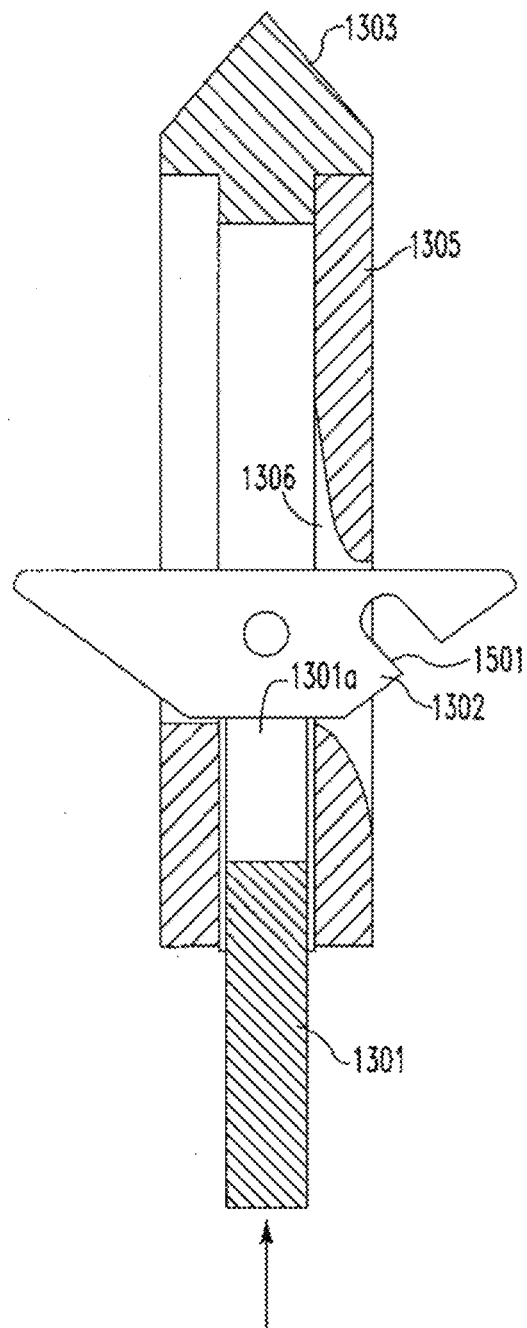
FIG. 15 is a diagram illustrating a configuration of a distal end portion according to a fifth embodiment of the present invention.

A fifth embodiment of the present invention will be described with reference to FIG. 15. FIG. 15 is a cross-sectional diagram of a distal end part of a drill bit according to the present embodiment. In the present embodiment, a thread insertion slit 1501 is provided in a blade 1502 in addition to the configuration of the fourth embodiment. After formation of a bone hole 1004, threads 1801 and 1802 for manipulating an endobutton 1702 are hooked on the thread insertion slit 1501, the blade 1502 is closed and the drill bit is pulled out, whereby the threads 1801 and 1802 can be pulled out of the body. In other words, a process during surgery can be further reduced.

REFERENCE SIGNS LIST

100 drill bit
101, 1104, 1301 shaft-like portion
102 grip
103 frame-like portion
104 rotational operation portion
105, 1103, 1305 tabular portion
106 mark
301, 1001, 1101, 1102, 1302, 1502 blade
203, 1303 distal end cutter
204, 1304 pin
205, 1105 protruded portion
901 block nut
902 guide portion
1501 thread insertion slit

What is claimed is:

1. A cutting instrument comprising:
   an elongated member including a tubular portion and a shaft-like portion inserted in the tubular portion;
   a blade provided at a distal end of the elongated member, the blade being pivotable between a housed position where the blade is housed in the elongated member and a projected position where an edge of the blade is projected outside the elongated member;
   an operation portion provided at a proximal end of the elongated member, the operation portion moving the tubular portion and the shaft-like portion relative to each other; and a motion mechanism that converts a relative movement of the tubular portion and the shaft-like portion resulting from an operation of the operation portion into pivoting of the blade between the housed position and the projected position,
   wherein the motion mechanism includes a groove portion provided in the blade and a protruded portion provided at the tubular portion, the protruded portion giving a pivoting force to the blade while moving within the groove portion, wherein the blade is a plate-like member including a first edge and a second edge at first and second positions, respectively, with a pivot axis centrally interposed there between.

2. The cutting instrument according to claim 1, wherein a center line of an edge surface of the first edge and a center line of an edge surface of the second edge lie on an identical straight line.

3. The cutting instrument according to claim 1, wherein a center line of an edge surface of the first edge and a center line of an edge surface of the second edge are parallel to one another.

4. The cutting instrument according to claim 1, wherein a center line of an edge surface of the first edge and a center line of an edge surface are non-parallel to one another.

5. The cutting instrument according to claim 1, wherein a center line of an edge surface of the first edge and a center line of an edge surface intersect at an oblique angle.

6. The cutting instrument according to claim 5, wherein first and second edges form oblique sides of a rough isosceles triangle shape of the blade.

7. The cutting instrument according to claim 1, wherein first and second edges of the blade are projected outside of the elongated member on opposing sides thereof when the blade is in the projected position.

8. The cutting instrument of claim 7, wherein the first and second edges of the blade are configured to be parallel to one another and perpendicular to a longitudinal axis of the elongated member, when the blade is in the projected position.

9. The cutting instrument of claim 7, wherein the first and second edges of the blade are configured to be at an oblique angle relative to a longitudinal axis of the elongated member, when the blade is in the projected position.

10. The cutting instrument of claim 7, wherein the first and second edges of the blade are configured to face proximally, when the blade is in the projected position.

11. The cutting instrument of claim 7, wherein the first and second edges of the blade are configured to face both proximally and laterally the longitudinal axis, when the blade is in the projected position.

12. The cutting instrument of claim 1, wherein blade is configured to enable drilling a first diameter in a first direction, when the blade is in the housed position, and a second diameter greater than the first diameter in a second direction, when the blade is in the projected position.

13. The cutting instrument of claim 1, wherein the blade is configured to enable drilling in a proximal direction when the blade is in the projected position.

14. The cutting instrument of claim 1, wherein the blade is configured to enable drilling in a distal direction when the blade is in the housed position.

15. The cutting instrument of claim 1, wherein the blade includes a pair of opposing blade parts which are symmetrically pivotable relative to the shaft, wherein each of the opposing blade parts includes a groove portion configured to interact with a respective protruded portion provided at the tubular portion, the protruded portion giving a pivoting force to the blade part while moving within the groove portion thereof.

16. The cutting instrument of claim 1, wherein the blade further defines a thread insertion slit.

* * * * *